United States Patent [19]
Brinton et al.

[11] Patent Number: 5,320,807
[45] Date of Patent: Jun. 14, 1994

[54] TEST KITS FOR DETERMINING THE CHEMICAL STABILITY OF A COMPOST SAMPLE

[76] Inventors: William F. Brinton, Old Rome Rd.; Mary D. Droffner, P.O. Box 145, both of, Mount Vernon, Me. 04352

[21] Appl. No.: 57,868

[22] Filed: May 7, 1993

[51] Int. Cl.⁵ .......................................... G01N 30/12
[52] U.S. Cl. ........................................ 422/61; 422/55; 422/66; 422/68.1; 422/69; 422/83; 422/85; 422/86; 436/29; 436/32; 436/33
[58] Field of Search ................. 422/55, 61, 66, 68.1, 422/69, 83, 85, 86; 436/29, 32, 33

[56] References Cited

U.S. PATENT DOCUMENTS

| | | | |
|---|---|---|---|
| 3,346,464 | 10/1967 | Ernst | 422/61 X |
| 3,702,755 | 11/1972 | Palmer | 422/55 X |
| 4,071,319 | 1/1978 | Nugent | 422/61 X |
| 4,269,804 | 5/1981 | Kring | 422/86 |
| 4,434,235 | 2/1984 | Rabi et al. | 436/110 |
| 4,533,519 | 8/1985 | Baugh et al. | 422/73 |
| 4,876,068 | 10/1989 | Castaneda | 422/58 |
| 4,877,580 | 10/1989 | Aronowitz et al. | 422/58 |
| 5,000,919 | 3/1991 | Heckmann | 422/58 |
| 5,013,668 | 5/1991 | Fields | 436/168 |
| 5,094,962 | 3/1992 | Snyder et al. | 436/518 |
| 5,096,813 | 3/1992 | Krumhar et al. | 435/28 |
| 5,128,102 | 7/1992 | Kaneko et al. | 422/56 |

Primary Examiner—Jill A. Johnston
Assistant Examiner—Harold Y. Pyon
Attorney, Agent, or Firm—Frederick R. Cantor

[57] ABSTRACT

A test kit for determining the 'total compost life', and chemical stability of a moist compost sample, includes a transparent container for holding the compost sample, and a reactant mass, located within the container in the space not occupied by the compost sample. The reactant mass includes a pH basic reactant material, and a color change indicator material, responsive to pH changes in the atmosphere within the container. After the moist compost sample is charged into the container, the container is sealed and allowed to remain undisturbed for a prescribed time period, e.g., about three (3) hours. During this time, carbon dioxide ($CO_2$) and volatile organic acids are emitted from the sample into the space surrounding the chemically reactant mass. The pH basic reactant chemically reacts with the emitted carbon dioxide ($CO_2$), in ionic form, or the emitted volatile organic acids, so as to produce a color change. The nature of the color change is an indication of the carbon dioxide ($CO_2$) content, or the volatile organic acids content in the compost sample.

6 Claims, 2 Drawing Sheets

TEST KITS FOR DETERMINING THE CHEMICAL STABILITY OF A COMPOST SAMPLE

BACKGROUND OF THE PRESENT INVENTION

The present invention relates to test kits that can be used to determine the 'total compost life', and the chemical stability of a selected compost sample. The test kit comprises a first reactant mass, that exhibits a color change in the presence of varying quantities of carbon dioxide ($CO_2$), whereby the test kit can be used to test for the carbon dioxide ($CO_2$) content in a compost sample. The test kit further comprises a second reactant mass that exhibits a color change in the presence of varying quantities of selected volatile organic acids, such that the kit can also be used to test for volatile organic acids content in a selected compost sample.

The test kit is especially designed for use by operators of facilities where digested sludge, leaves, and other waste products, are being aerobically transformed into useful compost, having value as a low nitrogen-content fertilizer. The test kit enables the operator of the facility to determine the point at which the compost is ready for drying, or curing.

Composting is a process of biological oxidation of organic materials, e.g., digested sludge, leaves, etc., whereby the materials are dewatered and deodorized into a finely divided condition, suitable for use as a fertilizer. The composting operation can be carried out by either the windrow-composting procedure, or the static pile composting procedure.

In the windrow composting procedure, the waste products are formed into elongated windrows, that are normally ten (10) to fifteen (15) feet wide, and five (5) feet, or more, in height. Periodically, a powered composting machine is driven slowly along the windrow, to lift, mix, and shred the organic materials, so that materials near the outer surface of the windrow, exchange places with materials in the interior zone of the windrow. The mixing and shredding action, also aerates the mixture, and redistributes moisture relatively evenly throughout the windrow cross-section. The moisture content is typically greater than fifty (50) percent, based on the weight of the water, in relation to the weight of the wet material.

Usually, the shredding and mixing operation, is performed on a daily basis, for the period required to bring the materials to a biologically stable condition, suitable for curing, i.e., drying to a moisture content less than forty (40) percent. Normally, a period of from between two (2) and four (4) weeks of biological activity, is required to bring the materials to a stable condition. Drying the stabilized material can then be accomplished by laying the material as a thin layer on the ground, or a paved surface, where it can be exposed to the sun.

In static pile composting, an elongated triangular cross-section pile of material is formed over an elongated perforated pipe. Periodically, air is drawn out of the pipe by a fan, whereby new air is forced into the compost pile, by the sub-atmospheric condition produced within the compost pile, around the pipe. Oxygen introduced into the compost pile acts to oxygenate, and biologically attack the compost pile materials.

With either type of composting procedure, the biological activity produces $CO_2$ gas, and minor quantities of various volatile organic acids, such as acetic acid and butyric acid. The presence of these volatile organic acids in the waste materials is an indicator of undesired anaerobic fermentation and instability. Such acids can be quite odorous and a cause of phtyo-toxicity, associated with poorly composted, or fermented, materials. The presence of a high $CO_2$ gas content in the compost materials, indicates that the composting process is incomplete, and that the material is biologically unstable.

The present invention relates to low cost test kits, that can be used by the facility operator to determine approximately the volatile organic acids content and the $CO_2$ content in the composted materials, whereby the operator can then make an informed decision as to ending the composting operation and initiating the drying, or curing, operation.

SUMMARY OF THE PRESENT INVENTION

The primary object of the present invention is to provide test kits that can be used to determine the 'total compost life', and chemical stability of a selected compost sample. The test kit comprises a first reactant mass, that exhibits a color change in the presence of varying quantities of carbon dioxide ($CO_2$), whereby the test kit can be used to test for the carbon dioxide ($CO_2$) content in a compost sample. The test kit further comprises a second reactant mass that exhibits a color change in the presence of varying quantities of selected volatile organic acids, such that the kit can also be used to test for volatile organic acids content in a selected compost sample.

The present invention contemplates a test kit for determining the 'total compost life', and the chemical stability of a moist compost sample. The test kit comprises a small container, or vial, adapted to contain, and fully enclose, a small compost sample, whereby $CO_2$ gas and volatile organic acids emitted by the compost sample are trapped within the container. A reactant mass is supported within the container, so as to be in contact with the emitted gases and acids, said reactant mass comprising a basic pH reactant material, e.g., sodium hydroxide (NaOH), and a color change material, responsive to pH changes in the atmosphere within the container.

The small container is left undisturbed for a period of time, e.g., about three (3) hours, during which time the chemical atmosphere within the moist compost sample interacts with the atmosphere within the container, whereby $CO_2$ gas, or volatile organic acids, diffuse out of the sample, into contact with the reactant mass. Chemical reactions occurring as a result of the diffusion process are visibly recorded as a color change in the color change material.

The test kit is comprised of two different kit constructions. In one of the test kit constructions, the color change material undergoes a color change in the pH range from about 6.8 to about 10.6. This kit construction is specifically designed to test for the $CO_2$ content in the compost sample. In a second test kit construction, the color change material undergoes a color change in the pH range from about 5.4 to about 7.6. This kit construction is designed to test for volatile organic acids content in the compost sample.

In summary, and in accordance with the above discussion, the foregoing objectives are achieved in the following embodiments.

1. A test kit for determining the chemical stability of a moist compost sample, comprising:

a container for holding a compost sample, so that the sample can occupy only a portion of the container space;

said container having an open mouth, for inserting the sample, and an operable closure, engageable with said mouth, for sealing the sample within the container;

a reactant support means, locatable within the container;

a reactant mass carried by said reactant support means in a container space not occupied by the compost sample;

said reactant mass comprising a basic pH reactant material, and a color change indicator material, responsive to pH changes in the atmosphere within said container; and said container having a transparent wall, whereby color changes in said indicator material can be observed, without opening said closure, or removing said reactant material from said container.

2. The test kit, as described in paragraph 1, wherein said color change indicator material, undergoes color changes in the pH range from about 6.8 to about 10.6, whereby said kit can be used to test for $CO_2$ content in said compost sample.

3. The test kit, as described in paragraph 2, wherein the basic reactant material comprises NaOH.

4. The test kit, as described in paragraph 4, wherein the basic reactant material further comprises $BaCl_2$.

5. The test kit, as described in paragraph 2, wherein said color change indicator material comprises a first substance undergoing a color change in the pH range from about 6.8 to about 8.2, and a second substance, undergoing a color change in the pH range from about 8.2 to about 10.6, whereby said material has any one of three colors, depending on the pH.

6. The test kit, as described in paragraph 1, wherein said color change indicator material undergoes a color change in the pH range from about 5.4 to about 7.6, whereby said kit can be used to test for volatile organic acids content, in said compost sample.

7. The test kit, as described in paragraph 6, wherein said basic reactant material comprises NaOH.

8. The test kit, as described in paragraph 6, wherein said color change indicator material, comprises a first substance, undergoing a color change in the pH range from about 5.4 to about 6.6, and a second substance, undergoing a color change in the pH range from about 6 to about 7.6, where by said color change material has any one of a multiple number of colors, depending on the pH.

9. The test kit, as described in paragraph 1, wherein said reactant support means comprises a flat blade, having a relatively shallow recess therein; and said reactant mass being located within said recess.

10. The test kit, as described in paragraph 9, wherein said shallow recess has a depth of about two (2) millimeters; and said reactant mass, being a flat patch of material filling said recess, whereby said patch has a thickness of no more than about two (2) millimeters.

11. The test kit, as described in paragraph 10, wherein said patch has a face area of about one (1) square inch.

12. The test kit, as described in paragraph 9, wherein said flat blade is suspended from said closure.

13. The test kit, as described in paragraph 1, wherein said reactant mass further comprises an inert carrier material; said reactant material and said color change indicator material being uniformly dispersed within said carrier material.

14. The test kit, as described in paragraph 13, wherein said carrier material is agar gel.

DESCRIPTION OF A PREFERRED EMBODIMENT OF THE PRESENT INVENTION

Figure 1:
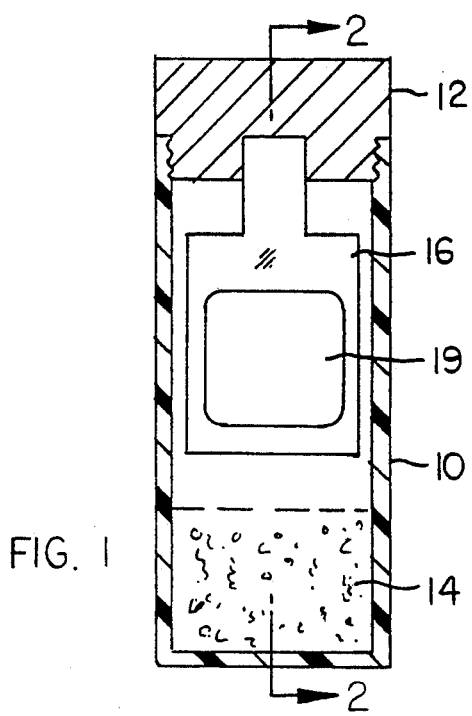
FIG. 1, is a sectional view, taken through a test kit, constructed according to the present invention

As noted previously, the present invention relates to a low cost test kit that can be used to determine the chemical stability of a moist compost sample. Two test kit constructions are employed herein. Each test kit construction includes a container for holding the moist compost sample, and a reactant mass, comprising a pH basic reactant material, e.g., NaOH, and a color change material, responsive to pH changes in the atmosphere within the container. The container has a transparent wall, whereby color changes in the indicator material can be observed, without opening the container, or removing the reactant mass. The reactant mass may be a thin patch of material, supported on a blade, or paddle, suspended within the transparent container, such that the colored patch can be readily seen through the transparent container wall.

Each test kit construction may be similarly constructed, except for the nature of the color change material. A kit designed to test for $CO_2$ content in the moist compost sample, will have a color change material designed to undergo color changes in the pH range from about 6.8 to about 10.6. A kit designed to test for volatile organic acids content in the moist compost sample, will have a color change material designed to undergo color changes in the pH range from about 5.4 to about 7.6. These pH ranges can be varied while still practicing the present invention, i.e., by using different color change substances.

Referring to the $CO_2$ respiration test, the test kit is designed to measure the rate of release of $CO_2$ gas from a moist compost sample, in a prescribed period of time, e.g. less than three (3) hours from the time that the compost sample is inserted into the container. The test is useful for compost producers who need to determine when a compost is finished and ready for market, i.e., when the compost is biologically stable. In the test container, the $CO_2$ diffuses from the compost sample into an agar gel carrier for a pH basic reactant material, and a pH responsive color change material. The $CO_2$ is trapped in the agar gel, resulting in a visual pH change, due to carbonic acid formation and reaction with the pH basic reactant.

The $CO_2$ respiration, or diffusion, test, contributes to understanding the 'total compost life', and the compost stability from a microbiological basis. The more advanced the composting process is, the less $CO_2$ respiration is observed. Information on $CO_2$ content, aids in deciding when true biological stability has been reached. Such information also can be used to estimate the nitrogen content, and the value of the compost, as a fertilizer.

$CO_2$ gas, released from a moist compost sample, reacts with water in the container atmosphere, to form carbonic acid, according to the following reaction:

$$CO_2 + H_2O \longrightarrow H_2CO_3$$

In the presence of sodium hydroxide (NaOH), the carbonic acid is neutralized, according to the following reaction:

$$H_2CO_3 + 2NaOH \longrightarrow Na_2CO_3 + 2H_2O$$

The sodium carbonate salt is moderately stable in the agar gel carrier matrix. However, there is some instability toward reaction with $H_2CO_3$, or other acids, that might be present. Such reverse reaction may be prevented by the addition of a small amount of barium chloride, or other barium salt. A barium carbonate precipitate is formed, according to the following reaction:

$$Na_2CO_3 + BaCl_2 \longrightarrow 2NaCl + BaCO_3$$

By adding $BaCl_2$, the desired reaction is driven more quickly to a desired end point, wherein color changes are produced in two pH color change substances, dispersed within the agar gel carrier matrix.

In a preferred test kit construction, two pH indicators are used. One color change substance is thymol blue, having a color change from blue to yellow in the pH range from about 10.6 to about 8.2. The second color change substance is rosalic acid, having a color change from red to yellow in the pH range from about 8.2 to about 6.8. When the two color change substances are combined, the color changes overlap, so as to provide three different colors, i.e., purple, orange, and yellow, depending on the pH. At a pH of about 10.6, the red from the rosalic acid, combines with the blue from the thymol blue, to produce purple. At a pH of about 8.2, the red from the rosalic acid combines with the yellow from the thymol blue, to produce orange.

FIG. 1, is a sectional view, taken through a test kit, constructed according to the present invention.

Figure 2:
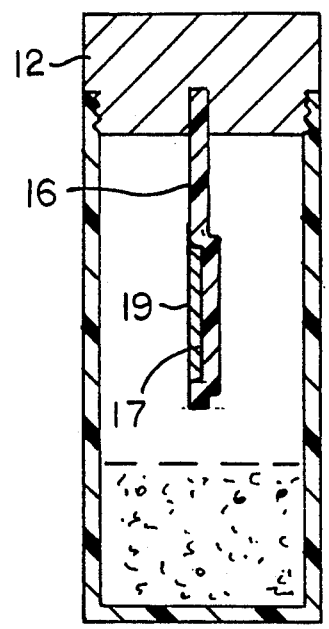
FIG. 2, is a sectional view, taken along line 2—2, in FIG. 1.

FIG. 2, is a sectional view, taken along line 2—2, in FIG. 1.

FIGS. 1 and 2, show a test kit embodying the present invention. A cylindrical container 10, is formed of a transparent plastic material, whereby the container interior space is readily seen through the transparent container side wall. The mouth of the container is threaded to have a screw fit with a removable closure, or cap 12. After opening the cap 12, a sample 14, of moist compost can be inserted into the container 10. A pre-determined quantity of compost is used, e.g., five (5) grams. For convenience, a gradation indicator may be provided on the side wall of the container 10, to measure the sample quantity on a volume basis.

Cap 12, carries a plastic blade 16, that extends downwardly within the container 10, in the space not occupied by the compost sample 14. A shallow recess 17, is formed in the flat side surface of the blade 16, to form a receptacle for a reactant mass, designated generally by numeral 19. Typically, recess 17, will have a depth of about two (2) millimeters, i.e., about eight-hundreths (0.08) of an inch. The reactant mass 19, will completely fill the recess 17, so that the surface of the reactant mass 19, is co-planar with the blade 16 surface. The relatively thin reactant patch 19, has a relatively large exposed surface area to volume ratio, whereby reaction with the carbonic acid is facilitated. The exposed surface area of the patch, as viewed in FIG. 1, may be about one (1) square inch.

Reactant patch 19, may be formed by pouring a heated reactant mixture into recess 17, using the recess 17, as a mold cavity. The reactant mixture can be prepared by a series of steps that includes the addition of barium chloride to a quantity of 0.05 normal NaOH, such that the barium chloride has a concentration of about eight (8) percent in the sodium hydroxide [NaOH]. Minor quantities of thymol blue and rosalic acid are added to the above solution, after which the solution is mixed with a two (2) percent Noble agar gel, that has previously been heated. The reactant solution and agar gel are mixed together on an equal volume basis. The heated mixture is then immediately poured into the mold cavity, i.e., recess 17, as seen in FIG. 2, and allowed to harden. The reactant patch can then be dried, or vacuum desiccated, to facilitate a smooth patch 19 surface. The addition of alcohol to the molded mixture can be used to prevent formation of a meniscus, on the edges of the patch.

Figure 3:
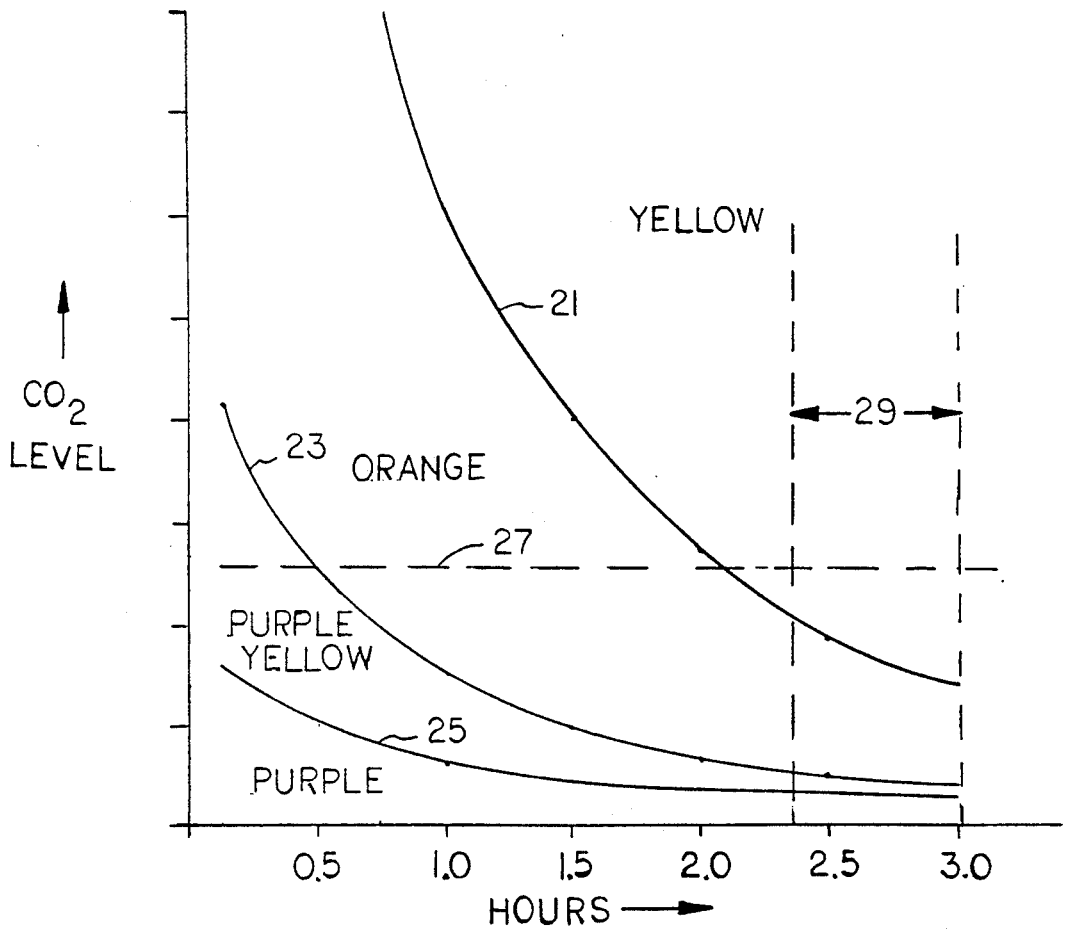
FIG. 3, is a chart, illustrating the performance of the test kit, depicted in FIG. 1.

FIG. 3, is a chart, illustrating the performance of the test kit, depicted in FIG. 1.

The test kit operates empirically, on the basis of calibration work, run with known compost compositions, i.e, known compost $CO_2$ contents. FIG. 3, shows generally how the test kit performs. The graph shown there, plots the $CO_2$ level in the moist compost sample versus elapsed time measured from the time when the compost sample is inserted into the container 10.

Initially, the indicator patch 19, will have a purple coloration, due to the NaOH content. As the container is allowed to remain undisturbed for a period of time, the coloration of the patch may change, depending on the quantity of $CO_2$ emitted from the compost sample 14, into the atmosphere within the container 10. Moisture emitted by the compost sample 14, combines with $CO_2$ in the container atmosphere to form carbonic acid. The carbonic acid reacts with the NaOH to produce a color change in reactant mass 19.

In FIG. 3, lines 21, 23, and 25, represent the demarcations between various colors produced on reactant patch 19. Depending on the $CO_2$ content, emitted by the compost sample 14, different colors may be achieved over a period of time. During the initial time period, i.e., up to about two (2) hours, the color may, or may not, undergo multiple color changes, depending on the $CO_2$ content. For example, with a $CO_2$ content designated by numeral 27, the color may change from purple to orange to yellow, depending on the time when a reading is taken. At about the three hour time period, essentially all of the $CO_2$ that can be emitted by the compost sample, will have been emitted, i.e., an equilibrium will have been established between the container atmosphere and the $CO_2$ diffusion out of the sample. Therefore, it is preferred to take the color reading near the three hour period. Numeral 29, designates a preferred time range for taking the reading.

As noted previously, a generally similar test kit can be constructed for testing the presence of volatile organic acids in a moist compost sample 14. Such acids commonly comprise acetic acid and butyric acid. The presence of such acids in significant amounts is an indicator of undesired anaerobic fermentation and biological instability of the compost. On a parts-per-million basis, volatile organic acids levels can be classified generally as follows:

| Rating | Acid Level [parts-per-million on a dry basis] |
| --- | --- |
| very low | <300 |
| medium low | 300–2,000 |
| medium | 2,000–4,000 |
| medium high | 4,000–10,000 |
| high | 10,000–20,000 |

Volatile organic acids levels above about 2,500 parts-per-million are undesirable. Values below that level are acceptable.

A test kit for volatile organic acids levels can be constructed generally similarly to the test kit shown in FIGS. 1 and 2, except that different pH responsive color change substances are used. In a preferred construction, two color change materials are used. One color change substance is bromo-thymol blue, having a color change from yellow to blue, at a pH range from 6.0 to 7.6. The second substance is methyl red, having a color change from red to yellow in the pH range from 5.4 to 6.6. The color changes overlap, so that multiple color changes are achieved, depending on the pH. Color combinations include blue, green, orange and yellow.

A reactant mass can be prepared, using a heated two (2) percent Noble agar gel as a carrier material. The bromothymol blue is mixed with the methyl red on an eight (8) to one (1) basis, after which the color change mixture is combined with an 0.01 normal NaOH solution and the heated agar gel. The heated mixture is poured into a mold cavity, i.e., recess 17 in FIG. 1, and allowed to cool.

Figure 4:
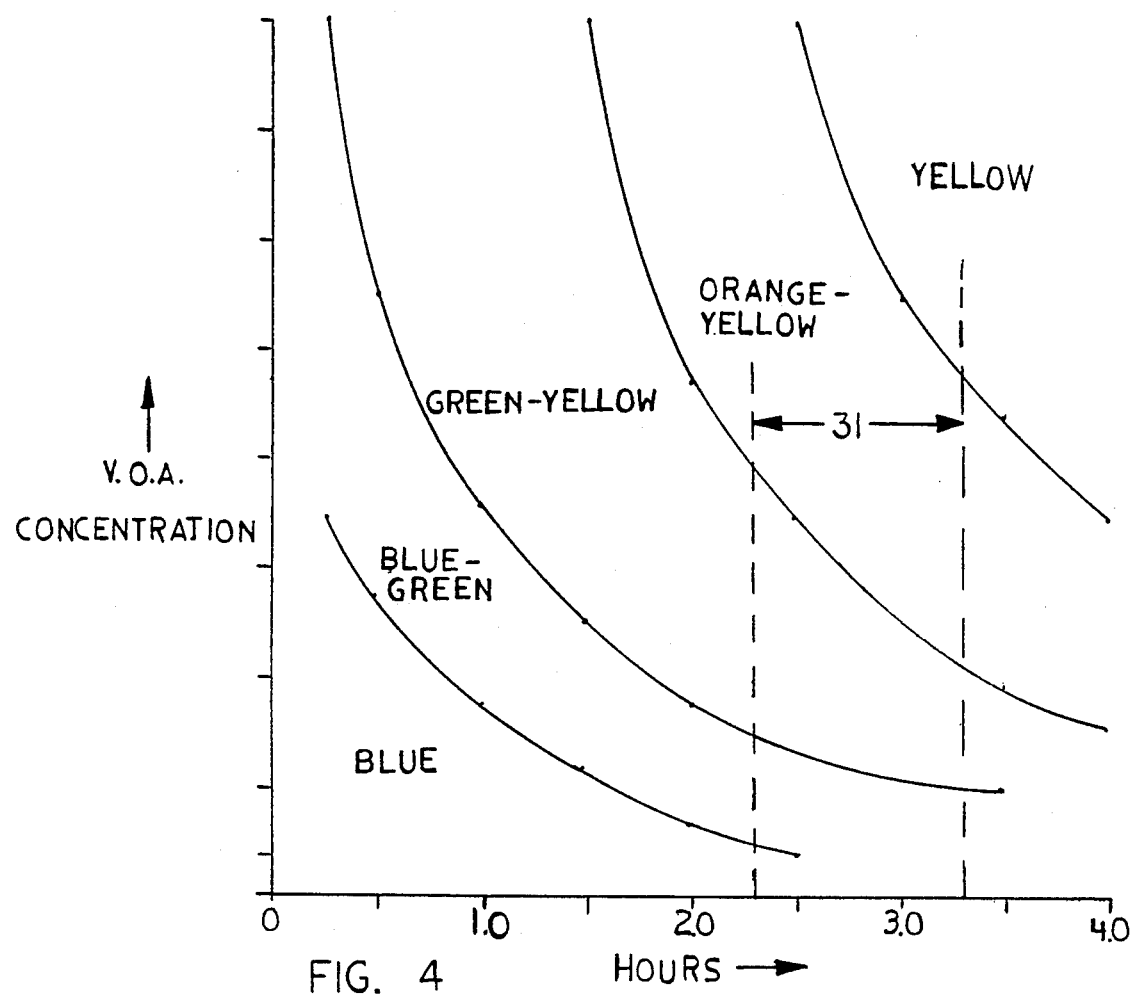
FIG. 4, is a chart, illustrating the performance of another test kit, incorporating features of the present invention.

FIG. 4, is a chart, illustrating the performance of another test kit, incorporating features of the present invention.

FIG. 4, is a graph, depicting the performance of the volatile organic acids test kit. Numeral 31, indicates the preferred time range, in which the color readings are to be taken.

Either test kit can include color charts, which are not shown, for aid in interpreting the meaning of the colors obtained on the reactant patches. As regards the $CO_2$ test, a color reading in the orange or purple area is considered acceptable. As regards the volatile organic acids test, a reading in the blue or green range is considered acceptable.

Figure 5:
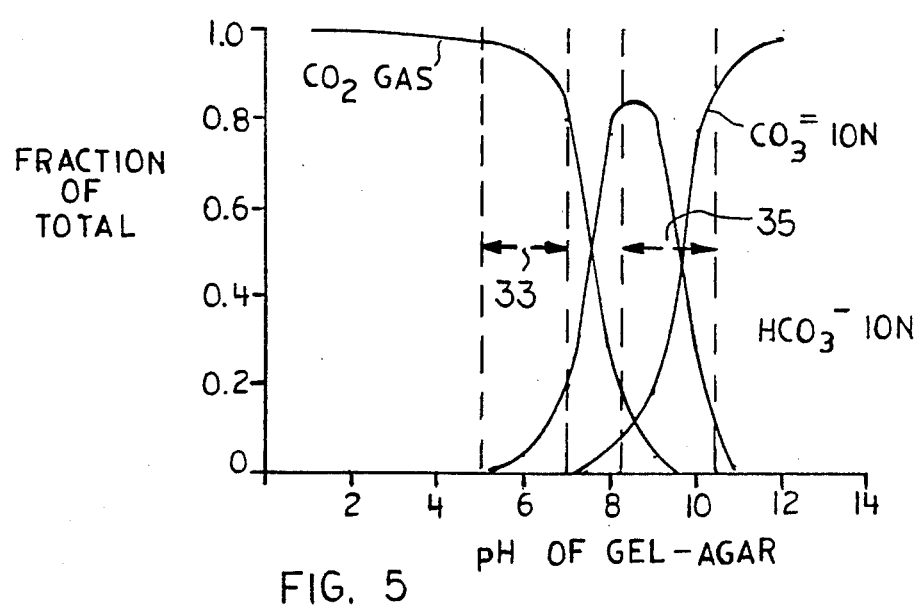
FIG. 5, is a graph, showing a relationship between pH and ionization of $CO_2$ into carbonate ionic form. The graph illustrates how the tests of FIGS. 3 and 4, can be carried out, without one test compromising, or distorting, the other test.

FIG. 5, is a graph, showing a relationship between pH and ionization of $CO_2$ into carbonate ionic form. The graph illustrates how the tests of FIGS. 3 and 4, can be carried out, without one test compromising, or distorting, the other test.

Since both tests utilize NaOH as a reactant, it might be supposed that the $CO_2$ test would, undesirably, also register, or record, the presence of the volatile organic acids, thereby mot providing a true indication of the $CO_2$ alone. Similarly, it might be supposed that the volatile organic acids test would undesirably measure the $CO_2$ content, along with the volatile organic acids content. However, it turns out that, because the two tests are run at different pH levels, the tests do not adversely affect, or compromise, either test results. The water solubility and dissociation of $CO_2$ is such, that, at a pH less than 7.0, virtually all of the $CO_2$ is in the gaseous, non-ionic state. $CO_2$ readings are taken at, or near, a pH of 8.0, with the $CO_2$ detected as dissolved $HCO_3^-$ or $CO_3^{--}$ ion. Attached FIG. 5, shows the general relationship between the different species, or states, of the $CO_2$ and the pH of the agar gel system.

The relatively high strength of the pH reactant base, i.e., NaOH, prevents any significant interference by the volatile organic acids in the $CO_2$ test results. The volatile organic acids are weak acids, and are present in relatively low amounts, significantly less than the $CO_2$. As regards the integrity of the volatile organic acids test, the $CO_2$ is in gaseous form at the pH levels where the volatile organic acids test is conducted, such that the presence of $CO_2$ is not detected by the volatile organic acids test. In FIG. 5, numeral 33 indicates generally the pH range encountered during the volatile organic acids test, and numeral 35, indicates generally the pH range of interest in the $CO_2$ test.

The present invention describes test kits for determining the 'total compost life', and the chemical stability of a compost sample. Features of the present invention are recited in the appended claims. The drawings herein necessarily depict specific structural and appearance features and embodiments of the test kits, and the chemical reactions, and associated color changes, useful in the practice of the present invention.

However, it will be appreciated by those skilled in the arts pertaining thereto, that the present invention can be practiced in various alternate forms and configurations. Further, the previously detailed descriptions of the preferred embodiments of the present invention, are presented for clarity of understanding only, and no unnecessary limitations should be implied therefrom. Finally, all appropriate mechanical, chemical, and functional equivalents to the above, which may be obvious to those skilled in the arts pertaining thereto are considered to be encompassed within the claims of the present invention.

What is claimed is:

1. A test kit for determining the carbon dioxide content and volatile organic acid content of moist compost comprising;

first and second containers for holding compost samples;

each container having an open mouth for inserting a compost sample, and an openable closure engageable with said mouth for sealing the sample within the respective container;

a reactant support means insertable into each container;

first and second reactant masses carried by respective reactant support means for disposition in the associated container;

each reactant mass comprising a color change indicator material responsive to pH changes in the atmosphere within said container;

the first reactant mass in said first container further comprising a basic pH reactant material, the color change material in said first reactant mass undergoing color changes in a basic pH range, whereby said first container can be used to test for the carbon dioxide content in the associated compost sample;

the color change material in said second reactant mass in said second container undergoing color changes in an acidic pH range, whereby said second container can be used to test for the volatile organic acid content in the associated compost sample;

each said container having a transparent wall, whereby color changes in the respective indicator materials can be observed without opening the respective closures; and a color standard for each reactant correlating the color thereof to the $CO_2$ and the volatile organic acid content respectively.

2. The test kit, as described in claim 1, wherein the color change indicator material in said first container undergoes color changes in the pH range from about 6.8 to about 10.6, and the color change indicator material in said second container undergoes color changes in the pH range from about 5.4 to about 7.6.

3. The test kit as described in claim 2, wherein the color change indicator material in said first container comprises a first substance undergoing a color change in the pH range from about 6.8 to about 8.2, and a second substance undergoing a color change in the pH range from about 8.2 to about 10.6; and said substances being selected so that the material formed thereby has any one of three colors, depending on the pH.

4. The test kit, as described in claim 2, wherein the color change indicator material in said second container comprises a first substance undergoing a color change in the pH range from about 5.4 to about 6.6, and a second substance undergoing a color change in the pH range from about 6.0 to about 7.6; and said substances being selected so that the material formed thereby has any one of a multiple number of colors, depending on the pH.

5. The test kit as described in claim 1, wherein each said reactant support means comprises a flat blade extended from the associated closure for disposition within the associated container; each said blade having two flat major faces viewable through the transparent wall of the associated container, and a shallow recess of appreciable area in one of said flat faces; and each said reactant mass being a flat patch of material filling the associated recess to a depth of no more than about two (2) millimeters.

6. The test kit as described in claim 1, wherein the basic reactant material in said first container comprises NaOH and a minor amount of barium chloride for forming a precipitate of barium carbonate when the reactant material is contacted by carbon dioxide in a moist atmosphere.

* * * * *